United States Patent [19]

Frank

[11] Patent Number: 5,064,259

[45] Date of Patent: Nov. 12, 1991

[54] APPARATUS FOR SCANNING A PHOTO-STIMULABLE PHOSPHOR SHEET

[75] Inventor: Lee F. Frank, Rochester, N.Y.

[73] Assignee: Eastman Kodak Company, Rochester, N.Y.

[21] Appl. No.: 588,779

[22] Filed: Sep. 27, 1990

Related U.S. Application Data

[63] Continuation-in-part of Ser. No. 446,246, Dec. 5, 1989, abandoned.

[51] Int. Cl.$^5$ .............................................. G02B 26/08
[52] U.S. Cl. ...................................... 350/6.5; 350/6.1
[58] Field of Search ................................. 350/486–487, 350/6.1–6.91, 612–617, 531; 250/327.2 A, 587.1, 234, 235, 236

[56] References Cited

U.S. PATENT DOCUMENTS

| | | | |
|---|---|---|---|
| Re. 31,847 | 3/1985 | Luckey | 250/327.2 A |
| 1,193,999 | 8/1916 | Dixon | 350/613 |
| 3,981,566 | 9/1976 | Frank et al. | 350/6.5 |
| 4,013,367 | 3/1977 | Nagao et al. | 350/6.9 |
| 4,093,340 | 6/1978 | Klose | 350/6.5 |
| 4,445,126 | 4/1984 | Tsukada | 350/6.5 |

Primary Examiner—Bruce Y. Arnold
Assistant Examiner—Thong Nguyen
Attorney, Agent, or Firm—William F. Noval

[57] ABSTRACT

Apparatus for scanning a photostimulable phosphor sheet includes a laser for forming a beam of stimulating radiation, and a photodetector for sensing radiation emitted from the sheet. An optical scanner scans the laser beam of stimulating radiation across the sheet to define a moving scanning spot and focuses light emitted from the phosphor sheet at the scanning spot onto the photodetector. The optical scanner includes a plurality of focusing mirror segments which are mounted to focus a spot on the phosphor sheet onto the photodetector and which are moveable for scanning the spot across the phosphor sheet with the beam of stimulating radiation being directed onto one of the mirror segments to focus on the spot.

5 Claims, 2 Drawing Sheets

APPARATUS FOR SCANNING A PHOTO-STIMULABLE PHOSPHOR SHEET

This is a Continuation-in-Part of U.S. Ser. No. 446,246; entitled Apparatus for Scanning a Photo-Stimulable Phosphor Sheet; filed Dec. 5, 1989; now abandoned.

TECHNICAL FIELD

The invention relates to apparatus for reading out the image stored in a photo-stimulable phosphor image recording medium, and more particularly to apparatus for detecting the radiation emitted from a photo-stimulable phosphor sheet in response to interrogation by stimulating radiation.

BACKGROUND ART

In the photo-stimulable phosphor imaging system, as described in U.S. Pat. No. Re. 31,847 reissued Mar. 12, 1985 to Luckey, a photo-stimulable phosphor sheet is exposed to an imagewise pattern of high energy short wavelength radiation, such as x-radiation, to record a latent image pattern in the photo-stimulable phosphor sheet. The latent image is read out by stimulating the phosphor with a relatively long wavelength stimulating radiation, such as red or infrared light. Upon stimulation, the photo-stimulable phosphor releases emitted radiation of an intermediate wavelength, such as blue or violet light, in proportion to the quantity of short wavelength radiation that was received. To produce a signal useful in electronic image processing, the photo-stimulable phosphor sheet is scanned in a raster pattern by a beam of light produced for example by a laser deflected by an oscillating or rotating scanning mirror, and the emitted radiation is sensed by a photodetector such as a photomultiplier tube, to produce the electronic image signal.

In more recent apparatus, the light emitted from the phosphor is collected by a wide aperture collector such as a mirror box or transparent collector, and sensed by a photomultiplier tube. Any persistent decay of the phosphor is detected by the wide aperture collector and degrades the signal produced by the apparatus.

SUMMARY OF THE INVENTION

In accordance with the present invention, the above-referenced shortcomings of photo-stimulable phosphor image scanning systems are obviated by apparatus having a light source for forming a beam of stimulating radiation; a photodetector for sensing radiation emitted from the phosphor sheet; and a scanner for scanning the beam of radiation across the sheet to define a moving scanning spot and for focusing the light emitted from the phosphor sheet in the vicinity of the scanning spot onto the photodetector. The scanner includes a plurality of focusing mirror segments and means for mounting the segments to image a spot on the sheet onto the photodetector and movable for scanning the spot across the sheet. The beam of stimulating radiation is directed onto one of the mirror segments to focus onto the spot on the phosphor sheet. In a preferred embodiment, the focusing mirror segments are formed of short lengths of cylindrical mirror strips and are pivotally supported in a linear, side-by-side configuration on mirror support linkages that are connected on one end to a support frame by respective flexure members. The other end of each support linkage is connected by a flexure to a drive linkage, the translation of which flexes the flexure members and pivots each support linkage and thereby simultaneously rotates each mirror segment. Each mirror segments has a narrow focus such that light rays from a point source incident on each of the mirror segments are effectively focused to a point location. All of the mirror segments are focused on the same point. As the mirror segments are simultaneously rotated by the translation of the drive linkage, the point on the surface of the photostimulated material that is formed on the photodetectors is translated along a line that is parallel to the direction of translation of the drive linkage.

The beam of stimulating radiation is reflected from a central one of the mirror segments and is scanned across the phosphor sheet when the drive linkage is moved. Since the scanning mirror assembly is employed to scan both the stimulating beam, and the light collection optics for the photodetector, the photodetector senses light from only a small area of the phosphor sheet in the vicinity of the scanning spot. Light emitted in other regions of the phosphor sheet due to persistent emission of the phosphor is not detected, thereby improving the signal to noise ratio of the detected signal.

In accordance with a preferred embodiment of the invention the focusing mirror segments are cylindrical mirror segments having cylindrical axes perpendicular to the surface of the phosphor sheet, and the scanner includes a pair of elliptical cylindrical mirrors having cylindrical axes parallel to the surface of the phosphor sheet and which relay light between the phosphor sheet and the photodetector via the segmented scanning mirror. The beam of stimulating radiation from the light source (e.g. laser) is directed to the central mirror segment through an aperture in one of the elliptical cylindrical mirrors, so that, as the mirror segments are rotated by the drive linkage, the projected spot will be scanned across the surface of the photo-stimulable material and thereby cause the emission of light rays from a surface region upon which the projected spot is incident.

In order to maintain better focusing of the scanning spot on the photodetector throughout the entire sweep of the scanner, the mirror drive linkage preferably is configured with a plurality of stepped connection portions, respectively coupled to different ones of the mirror support linkages and the mirror support linkages at the ends of the array are slightly longer, such that mirror segments on the ends of the segmented mirror array are scanned through slightly smaller angles than those in the middle of the array. Scanning successive traces across the phosphor material is effected by translating the phosphor material in a direction different than (substantially orthogonal to) the direction of scan of the mirror segments by the mirror drive linkage.

DETAILED DESCRIPTION

Figure 1:
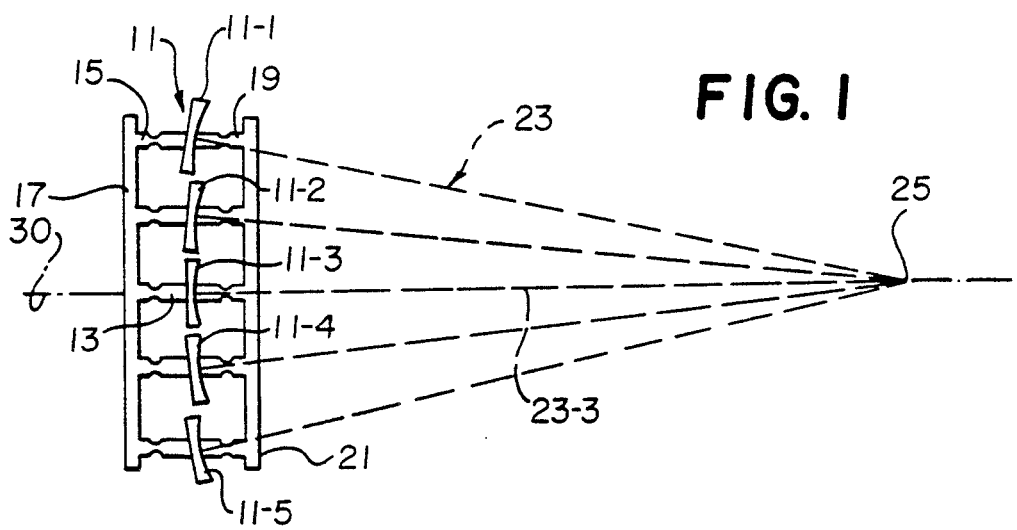
FIG. 1 is a plan view of the segmented focusing mirror portion of a mirror scanning apparatus in accordance with the present invention.
Figure 2:
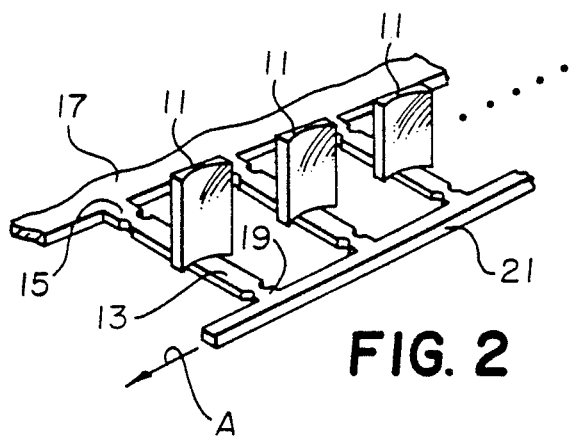
FIG. 2 is a partial perspective view of the arrangement of the cylindrical mirror segments of the scanner of FIG. 1.
Figure 3:
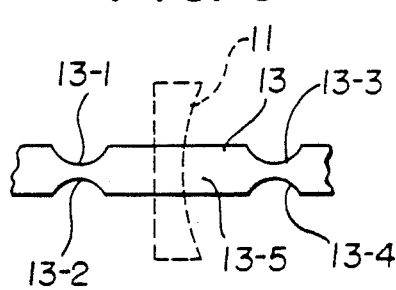
FIG. 3 is a top view of an individual mirror support linkage and flexure members.

Referring now to FIG. 1 of the drawings, a top or plan view of the segmented focusing mirror portion of a stimulable phosphor scanning apparatus in accordance with the present invention is shown diagrammatically as containing a plurality of cylindrical mirror segments 11, five of which 11-1, 11-2, 11-3, 11-4 and 11-5 are illustrated in FIG. 1, to simplify the illustration. It should be observed that the number of mirrors shown (five) is merely for purposes of providing an illustrative example and is not limitative of the invention. As shown in FIG. 1 and in the partial perspective view of FIG. 2, the cylindrical mirror segments 11 are pivotally supported in an equally spaced, side-by-side configuration by way of respective parallel mirror support linkages 13 (a top view of an individual one of which is shown in detail in FIG. 3). One end 15 of each mirror support linkage 13 is connected to a support frame or bar 17, and the other end 19 is connected to a mirror drive linkage 21. Also, as shown in FIGS. 2 and 3, each mirror support linkage 13 may be a generally rectangular rod, with respective pairs of concave recess or reduced thickness regions 13-1, 13-2, and 13-3, 13-4 adjacent respective opposite ends of the rod. The reduced thickness regions provide flexures for pivoting the central region of the linkage 13. A respective mirror segment 11 is mounted at a generally central region 13-5 (FIG. 3) of the mirror support linkage. The mirror segment 11 may be fixed to the mirror support linkage 13, for example, by epoxy. As a consequence, moving drive linkage 21 in the direction of arrow A in FIG. 2 will cause the reduced thickness regions 13-1, 13-2, and 13-3, 13-4 to bend and the central region 13-5 to pivot with respect to ends 15 and 19 thereby causing the mirror segment 11 it supports to be pivoted or rotated. The slight translation of the mirror segment 11 that will also result can be ignored, as it has not been found to degrade the performance of the scanner.

The linkage 21 is shown in FIG. 1 as a thin rectilinear bar, which extends in a direction parallel to support frame 17. The translation of which linkage 21 simultaneously flexes the flexures and pivots each mirror support linkage 13. Each mirror segment 11 is thereby rotated to effect a scanning or sweep of the focal point of each mirror segment 11. In a preferred embodiment of the invention, the support frame 17, mirror support linkage 13 and mirror drive linkage 21 are formed from a single sheet of metal (e.g. aluminum) for example by chemical milling; and the cylindrical mirror segments 11 are attached to the central regions 13-5 of the mirror support linkages 13 with epoxy resin. The cylindrical mirror segments 11 are preferably silvered glass mirrors. However weight reductions in the apparatus may be achieved by forming the cylindrical mirror segments 11 from diamond machined aluminum.

Figure 4:
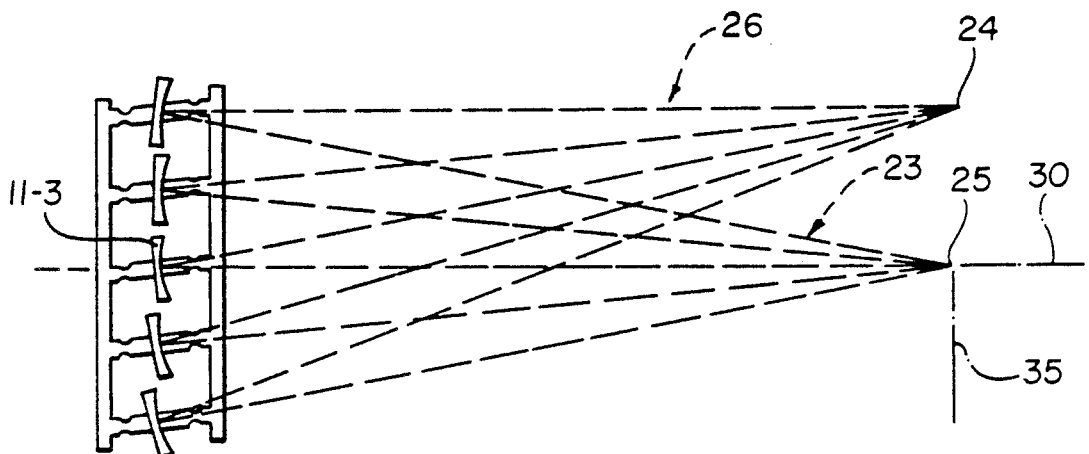
FIG. 4 shows the translation of the mirror drive linkage and resulting change in focal point of the scanner.

Referring to FIG. 1, the mounted orientation of each cylindrical mirror segment 11 on mirror support linkage 13 is such that light rays 23 emanating from a point light source 25 and incident on each of the mirror segments 11 are focused at a common location in space. In the diagrammatic plan view illustration of FIG. 1, a ray 23-3 from point light source 25 and incident on a central one 11-3 of the group of five mirror segments 11-1, 11-2, 11-3, 11-4, and 11-5 is focused at point light 25. Similarly, in the positional configuration shown in FIG. 1, mirror segments 11-1, 11-2 are oriented symmetrically with respect to mirror segment 11-5, 11-4, respectively, on opposite sides of central mirror segment 11-3, so as to focus respective ones of rays 23 incident thereon from point light source 25 back to point light source 25, which lies on a central axis of symmetry 30 of the mirror segments 11. As shown in FIG. 4, the translation of linkage bar 21 upwardly in the Figure or to the right of the central axis 30 as viewed from point light source 25, simultaneously pivots each mirror segment 11 counter-clockwise, so that the reflected light rays 26 are focused toward an imaging location 24 lying along a scanning axis 35, passing through point light source 25.

As pointed out above, the scanning mechanism of the present invention is employed for the scanning of a radiographic image that has been captured on a planar layer of photo-stimulable material, such as a phosphor plate. In such an application, scanning axis 35 traverses the phosphor plate, so that as mirror segments 11 are simultaneously rotated by pivoting the mirror support linkages 13, the light rays emitted by a light source at point 25 are focused by the mirror segments 11 to point 24, and point 24 is scanned across the phosphor plate as the mirror drive linkage 21 is moved. Since the rotational inertia of the mirror segments 11 is relatively small, high speed scanning of the photo-stimulable phosphor sheet can be accomplished.

Although mirror segments 11 will focus light emitted from a point 25 to a point 25 on axis 35 when simultaneously pivoted by mirror drive linkage 21, the fact that each mirror support linkage 13 undergoes the same degree of rotation causes an aberration in the focused light, particularly at the extreme ends of the scan on either side of central axis 30 (i.e., the light rays from each mirror do not focus exactly at point 25). To minimize this problem and maintain a high degree of focus of the rays throughout the entire range of the scanner, the mirror drive linkage 21, rather than being formed as a thin straight bar as shown in FIG. 1, is preferably configured as shown in FIG. 5 in the form of a stepped bar 41, having a plurality of sequentially offset, or stepped, portions 41-1, 41-2, 41-3, 41-4, and 41-5.

By virtue of these stepped portions, which are respectively rigidly fixed to the ends 19 of successive ones of mirror support linkages 13, mirror support linkages 13 are of respectively different lengths. Consequently, the angle through which each mirror support linkage 13 is pivoted and therefore the angle of rotation of each mirror segment 11 will be different from that of an adjacent mirror segment 11 during the translation of stepped mirror drive linkage 41. This additional degree of freedom, coupled with the ability to mount each mirror segment 11 on its mirror support linkage 13 at any orientation and the ability to set the distance from a stepped portion 41 of the drive linkage to the support frame 17 provide three degrees of freedom for minimizing error in the registration of the rays focused by the mirror segments 11.

Figure 5:
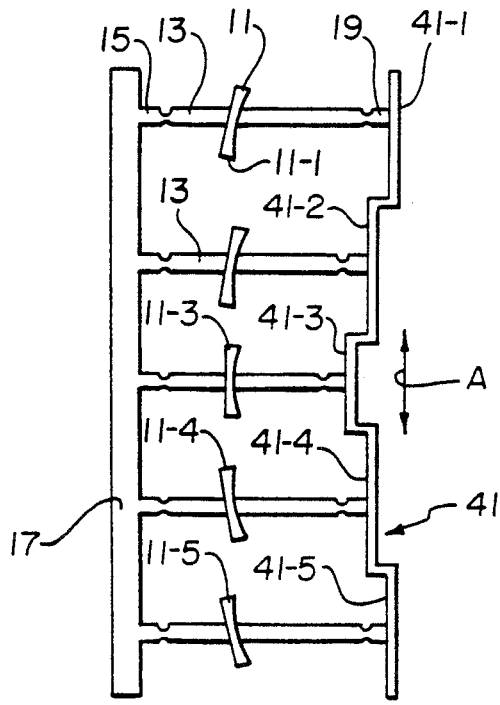
FIG. 5 shows a mirror drive linkage configured in the form of a stepped bar with mirror support linkages of different lengths.

As can be appreciated from FIG. 5, when mirror drive linkage 41 is displaced in the direction of arrow A, the mirror support linkages 13 will exert a bending force on mirror drive linkage 41 due to their unequal lengths. To relieve the stress thus induced, mirror drive linkage 41 is constructed to be thin enough to bend in response.

Figure 6:
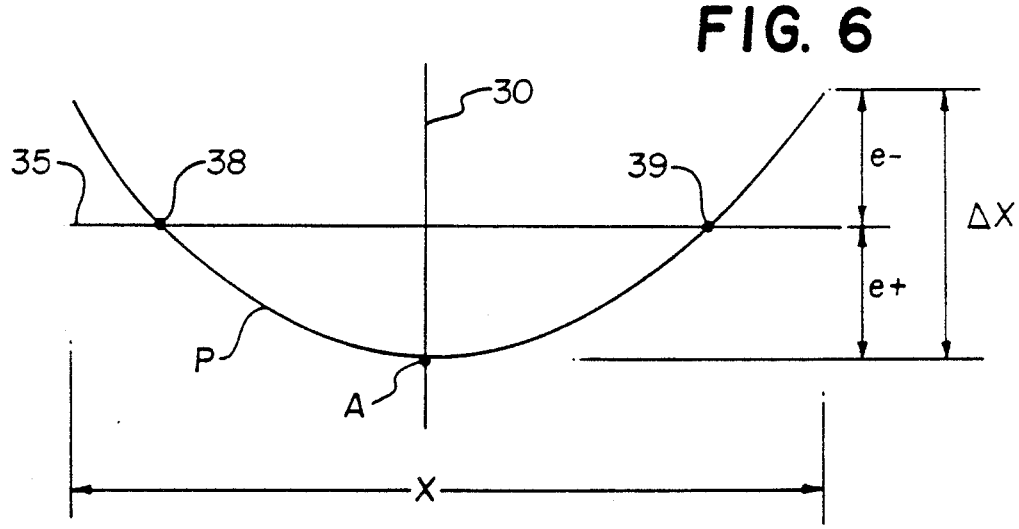
FIG. 6 shows a locus of the focal point of the scanner using the stepped bar mirror drive linkage of FIG. 5.
Figure 7:
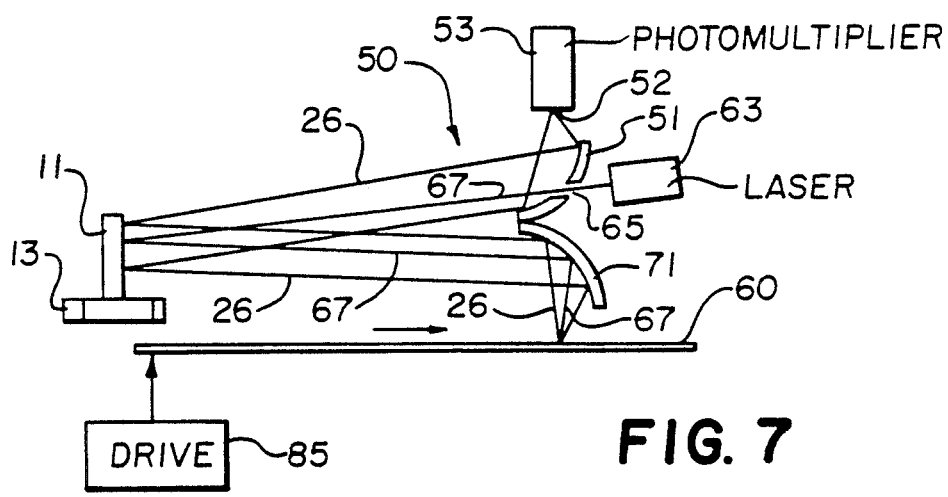
FIG. 7 diagrammatically shows the coupling of the mirror segments of the scanner of FIG. 1 with a pair of elliptical cylindrical mirrors, for scanning a translated phosphor screen.

In order to minimize focusing error due to spherical aberration, rather than orient the mirror segments 11 symmetrically on either side of center line 30 such that the focused rays from each of the mirror segments 11 come into registration at the intersection of center line 30 and the surface of the scanned phosphor plate, it is preferred that the mirror segments 11 be oriented such that their respective focal points come into registration with one another at spaced apart locations on either side of the center line 30. Specifically, as shown in FIG. 6, the locus of focal registration follows a parabola P, the apex A of which is coincident with center line 30. Rather than orienting the mirror segments 11 such that the apex A is located at the phosphor plate surface, the mirror segments 11 are positioned so as to displace the center line focus away from the plate surface, thus creating, relative to the focal registration locus P, an equal maximum aberration or error component $e-$ and $e+$ on either side of the scanning axis 35 across the phosphor plate. The geometry is such that locus parabola P intersects scanning axis 35 on the phosphor plate at points 38 and 39 each of which is displaced from center line 30 at a distance on the order of seven tenths of the distance from center line 30 to the end of the scan.

When scanning a photo-stimulable phosphor plate, it is necessary to provide ray projection optics between the scanned surface, the segmented scanning mirrors and the photodetector, so that the scanned surface may be translated orthogonally with respect to the scanner, thereby effecting a zig-zag scan along the surface of the image plate. Additional cylindrical mirrors are provided between the scanning mirror 11 and the photodetector (e.g. photomultiplier tube 53), so that the photomultiplier 53 may be positioned out-of-plane (orthogonal) with respect to the scanning mirror segments 11.

More particularly, as diagrammatically illustrated in FIG. 6, in order to perform scanning in an orthogonal direction, the cylindrically contoured mirror segments 11 of the scanner are optically coupled with a dual elliptical mirror projector 50, which includes a first elliptical reflector 71 that receives rays 26 emitted from the surface of a phosphor sheet 60 and directs the rays to scanning mirror segments 11. The rays 26 are focused by mirror segments 11 and projected by a second elliptical reflector 51 onto the entry window 52 of the light detector (e.g. photomultiplier) 53. The elliptical reflectors 51 and 71 are substantially as wide as the phosphor sheet 60. The elliptical reflector 51 and 71 may comprise silvered glass, or preferably diamond machined aluminum. In order to read out a radiographic image stored on a photo-stimulable phosphor sheet 60, a narrow beam of light from a source (e.g. laser) 63 is projected through an aperture 65 in the elliptical reflector 51 and, through this aperture, directs a 'spot' beam 67 of light onto central mirror segment 11-3, so that, as the mirror segments 11 are simultaneously rotated by the mirror drive linkage 21, beam 67, which is reflected by the second elliptical reflector 71, will be scanned across the surface of the phosphor sheet 60. In response to the incidence of 'spot' beam 67, sheet 60 emits rays 26, which are projected by elliptical reflector 71 onto scanning mirror segments 11 and focused thereby onto the photomultiplier 53. As the spot is scanned across the phosphor sheet 60, a drive mechanism 85 moves sheet 60 in a direction transverse to the back and forth scan of the 'spot' beam across the screen 60, so as to effect a successive zig-zag scan of the phosphor sheet 60.

Namely, as the respective mirror segments 11 of the scanner are simultaneously rotated by the action of the stepped mirror drive linkage 41, central mirror 11-3 focuses the spot beam 67 onto the phosphor sheet 60, while each of the mirror segments 11 receives light rays 26 emitted from successively scanned locations of the surface of phosphor sheet 60 and projected onto elliptical reflector 71 as the result of the stimulation of the phosphor sheet 64 by the scanned 'spot' beam from laser source 63. Each mirror segment 11 focuses these rays toward elliptical reflector 51 of projector 50, which projects the focused rays onto photomultiplier 53. Since the same scanning optics are used for both 'spot' beam 67 and for collecting the emitted rays from the phosphor sheet 60, registration of the stimulation scan with the area of collection of emitted light is assured.

As will be appreciated from the foregoing description, very small changes in the rotational position of each mirror element will result in a relatively large excursion of the scanned focal point, so that high speed scanning of the surface of the photo-stimulable material can be accomplished.

I claim:

1. Apparatus for scanning a photostimulable phosphor sheet, comprising:
   a. means for forming a beam of stimulating radiation;
   b. photodetector means for sensing radiation emitted from said sheet; and
   c. scanner means for scanning said beam of stimulating radiation across said sheet to define a moving scanning spot and for focusing light emitted from said phosphor sheet at said scanning spot onto said photodetector means, said scanner means including,
      1) a plurality of focusing mirror segments, and
      2) mounting means for mounting said mirror segments to focus light emitted from a spot on said sheet onto said photodetector means and moveable for scanning said spot across said sheet, said beam of stimulating radiation being directed onto one of said mirror segments to focus on said spot; wherein said mounting means include a plurality of mirror support linkages having a first end connected to a support frame by respective flexure members, and a second end connected to a mirror drive linkage by respective flexure members; and wherein said support linkages are of different lengths, and said mirror drive linkage is stepped and flexible.

2. Apparatus for scanning a photostimulable phosphor sheet, comprising:
   a. means for forming a beam of stimulating radiation;
   b. photodetector means for sensing radiation emitted from said sheet; and
   c. scanner means for scanning said beam of stimulating radiation across said sheet to define a moving scanning spot and for focusing light emitted from said phosphor sheet at said scanning spot onto said photodetector means, said scanner means including,
      1) a plurality of focusing mirror segments, and
      2) mounting means for mounting said mirror segments to focus light emitted from a spot on said sheet onto said photodetector means and moveable for scanning said spot across said sheet, said beam of stimulating radiation being directed onto one of said mirror segments to focus on said spot; further comprising a first elliptical mirror positioned between the stimulable phosphor sheet and said scanner means, and a second elliptical mirror positioned between said scanner means and said photodetector means, whereby light emitted from the stimulable phosphor sheet is directed to said scanner means and thence to said photodetector means.

3. The apparatus claimed in claim 2, wherein said second elliptical mirror defines an aperture through which said beam of stimulating radiation is directed onto said one of said mirror segments.

4. Apparatus for scanning a photostimulable phosphor sheet, comprising:
 a. means for forming a beam of stimulating radiation;
 b. photodetector means for sensing radiation emitted from said sheet; and
 c. scanner means for scanning said beam of stimulating radiation across said sheet to define a moving scanning spot and for focusing light emitted from said phosphor sheet at said scanning spot onto said photodetector means, said scanner means including,
  1) a plurality of focusing mirror segments, and
  2) mounting means for mounting said mirror segments to focus light emitted from a spot on said sheet onto said photodetector means and moveable for scanning said spot across said sheet, said beam of stimulating radiation being directed onto one of said mirror segments to focus on said spot; wherein said mounting means include a plurality of mirror support linkages having a first end connected to a support frame by respective flexure members, and a second end connected to a mirror drive linkage by respective flexure members; and wherein said support frame, mirror support linkages, flexures and mirror drive linkage are formed from a single sheet of flexible material.

5. The apparatus claimed in claim 4, wherein said flexible material is aluminum.

* * * * *